(12) United States Patent  (10) Patent No.: US 8,298,494 B2
Komiya et al.  (45) Date of Patent: Oct. 30, 2012

(54) ENDOSCOPE CLEANING/DISINFECTING APPARATUS CONNECTOR AND ENDOSCOPE CLEANING/DISINFECTING APPARATUS

(75) Inventors: Takaaki Komiya, Hachioji (JP); Masayoshi Aono, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/204,115

(22) Filed: Aug. 5, 2011

(65) Prior Publication Data

US 2012/0031506 A1 Feb. 9, 2012

Related U.S. Application Data

(63) Continuation of application No. PCT/JP2011/061098, filed on May 13, 2011.

(30) Foreign Application Priority Data

Aug. 3, 2010 (JP) .................................. 2010-174701

(51) Int. Cl.
*A61L 2/16* (2006.01)
*B08B 9/00* (2006.01)
(52) U.S. Cl. ................. 422/292; 134/166 R; 134/166 C
(58) Field of Classification Search .................. 422/292; 134/166 R, 166 C
See application file for complete search history.

(56) References Cited

U.S. PATENT DOCUMENTS

| 6,681,783 B2 * | 1/2004 | Kawazoe .................. 134/169 C |
| 2006/0269442 A1 | 11/2006 | Nguyen et al. |
| 2009/0205687 A1 | 8/2009 | Onishi et al. |
| 2010/0004510 A1 | 1/2010 | Kuroshima |

FOREIGN PATENT DOCUMENTS

| EP | 1 728 466 A2 | 12/2006 |
| EP | 2 098 185 A1 | 9/2009 |
| JP | 58-192525 | 11/1983 |
| JP | 2004-135946 | 5/2004 |
| JP | 2006-334405 | 12/2006 |
| JP | 2009-195400 | 9/2009 |
| JP | 2010-011977 | 1/2010 |

* cited by examiner

*Primary Examiner* — Sean E Conley
(74) *Attorney, Agent, or Firm* — Scully, Scott, Murphy & Presser, P.C.

(57) ABSTRACT

An endoscope cleaning/disinfecting apparatus connector according to the present invention includes a cleaning/disinfecting apparatus connection section, a circulating section and a discharge section, wherein the discharge section communicates with the circulating section and includes a first channel that discharges a fluid R that passes through the circulating section into a pipe sleeve, a second channel that branches from the first channel and discharges the fluid R to the periphery of the pipe sleeve, and an opening/closing section that is provided in a branch section that branches from the first channel to the second channel or in the second channel, is freely expandable/contractible according to a flow rate of a fluid and blocks the second channel when the flow rate of the fluid is a predetermined amount or higher.

2 Claims, 6 Drawing Sheets

ENDOSCOPE CLEANING/DISINFECTING APPARATUS CONNECTOR AND ENDOSCOPE CLEANING/DISINFECTING APPARATUS

CROSS REFERENCE TO RELATED APPLICATION

This application is a continuation application of PCT/JP2011/061098 filed on May 13, 2011 and claims benefit of Japanese Application No. 2010-174701 filed in Japan on Aug. 3, 2010, the entire contents of which are incorporated herein by this reference.

BACKGROUND OF THE INVENTION

1. Field of the Invention

The present invention relates to an endoscope cleaning/disinfecting apparatus connector that connects an endoscope and an endoscope cleaning/disinfecting apparatus, and an endoscope cleaning/disinfecting apparatus.

2. Description of the Related Art

When cleaning or disinfecting the interior of an endoscope tube using a cleaning/disinfecting apparatus, the operator connects a cleaning/disinfecting apparatus connection section provided at one end of an endoscope cleaning/disinfecting apparatus connector to a fluid supply port of the endoscope cleaning/disinfecting apparatus first. Furthermore, the operator connects a discharge section provided at another end of the endoscope cleaning/disinfecting apparatus connector to a pipe sleeve of the endoscope tube such as an air/water supply tube and a suction tube provided inside the endoscope, formed on an outer surface of the endoscope.

As a result, a fluid such as cleaning liquid, disinfecting liquid, rinsing water, gas is supplied from the endoscope cleaning/disinfecting apparatus into the endoscope tube through the endoscope cleaning/disinfecting apparatus connector and an opening of the pipe sleeve and the interior of the endoscope tube is thereby cleaned/disinfected.

Here, to prevent a fluid from leaking from the discharge section connected to the pipe sleeve, the discharge section has been provided with a leak prevention member such as an O-ring. However, in recent years, a configuration has been well known which provides no leak prevention member at the discharge section and intentionally causes a small amount of fluid to leak from a gap between the pipe sleeve and the discharge section so that the pipe sleeve and the periphery of the pipe sleeve may be cleaned/disinfected using the leaked fluid during a cleaning/disinfecting process by the cleaning/disinfecting apparatus.

For example, Japanese Patent Application Laid-Open Publication No. 2009-195400 discloses a technique providing an opening/closing valve that freely comes into contact with an opening edge of a pipe sleeve in a discharge section of an endoscope cleaning/disinfecting apparatus connector connected to the pipe sleeve of an endoscope and normally remains in non-contact with the opening edge by means of an urging force of a spring. When a fluid is supplied into the discharge section at a predetermined flow rate or higher, the opening/closing valve moves in the direction of the pipe sleeve against the urging force of the spring, thereby water-tightly and airtightly contacts the opening edge of the pipe sleeve and when the fluid is supplied into the discharge section at a flow rate less than the predetermined flow rate, the opening/closing valve moves apart from the pipe sleeve by means of the urging force of the spring and is kept in non-contact with the opening edge of the pipe sleeve.

SUMMARY OF THE INVENTION

An endoscope cleaning/disinfecting apparatus connector according to one aspect of the present invention is an endoscope cleaning/disinfecting apparatus connector that connects an endoscope and an endoscope cleaning/disinfecting apparatus and includes a cleaning/disinfecting apparatus connection section connected to the endoscope cleaning/disinfecting apparatus, a circulating section, one end of which communicates with the cleaning/disinfecting apparatus connection section, and in which a fluid supplied from the cleaning/disinfecting apparatus circulates, and a discharge section that is provided at another end of the circulating section, is freely connectable to a pipe sleeve of the endoscope, remains inside the pipe sleeve after the connection and thereby discharges the fluid which passes through the circulating section to the endoscope, wherein the discharge section includes a first channel that communicates with the circulating section and discharges the fluid that passes through the circulating section into the pipe sleeve of the endoscope and an opening/closing section that is provided between the first channel and an inner wall of the pipe sleeve, is freely expandable/contractible according to a flow rate of the fluid, expands when the flow rate of the fluid is a predetermined amount or higher, and closes a second channel that discharges the fluid discharged from the first channel and located between the first channel and the inner wall of the pipe sleeve to a periphery of the pipe sleeve of the endoscope, and the discharge section includes a water control section that is provided in the first channel and repels the flow of the fluid and an opening that is provided in the first channel and exhausts the fluid repelled by the water control section.

Furthermore, an endoscope cleaning/disinfecting apparatus according to one aspect of the present invention is provided with the endoscope cleaning/disinfecting apparatus connector according to the above described one aspect.

DETAILED DESCRIPTION OF THE PREFERRED EMBODIMENTS

Hereinafter, embodiments of the present invention will be described with reference to the accompanying drawings. It should be noted that the drawings are schematic ones and a relationship between the thickness and the width of each member and the ratio of thickness or the like among the respective members are different from the real ones and it goes without saying that the drawings also include parts whose dimensional relationships and ratios are different among the drawings.

(First Embodiment)

Figure 1:
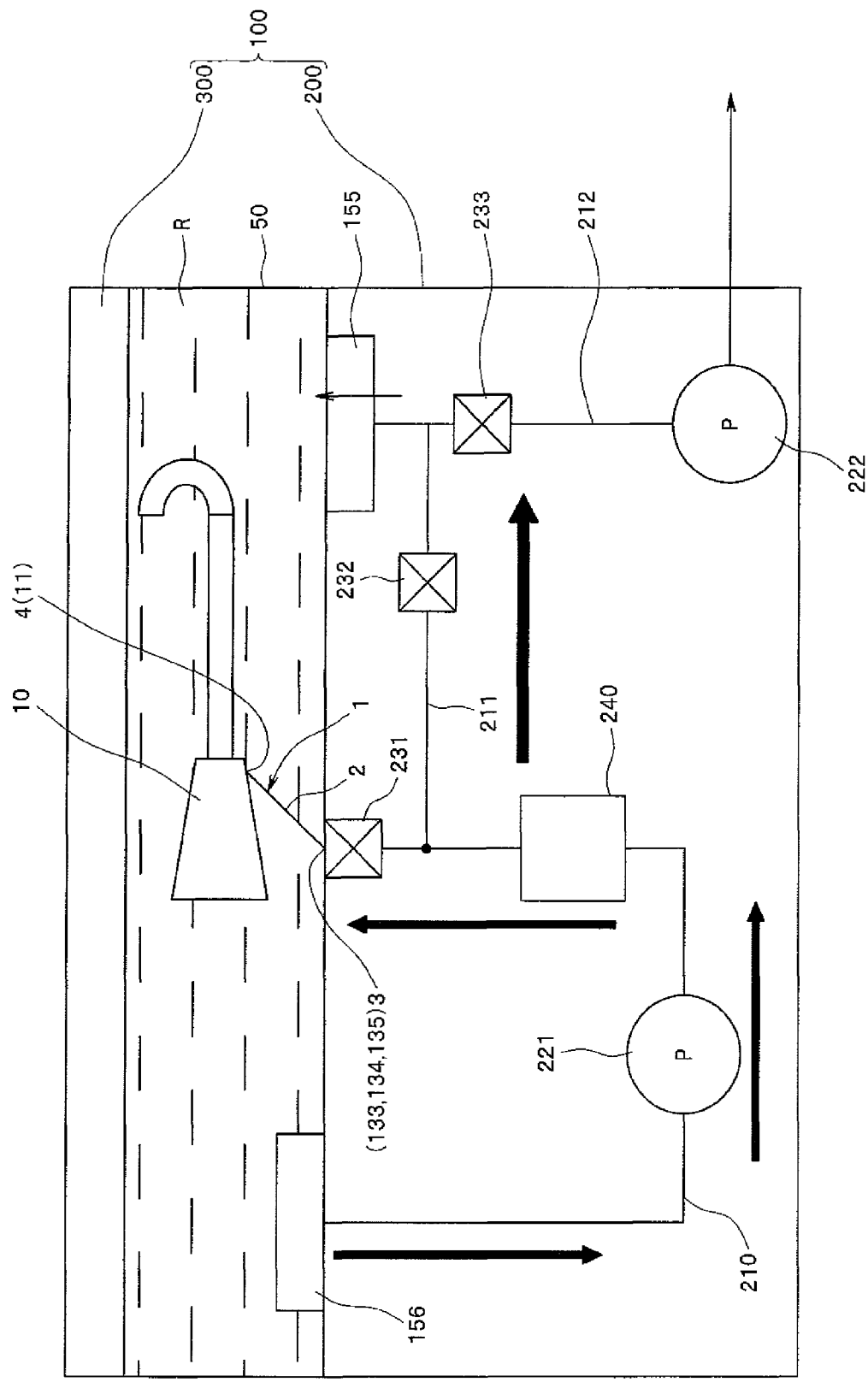
FIG. 1 is a diagram schematically illustrating an endoscope cleaning/disinfecting apparatus provided with an endoscope cleaning/disinfecting apparatus connector according to an embodiment with an endoscope immersed in a liquid stored in a cleaning/disinfecting tank.
Figure 2:
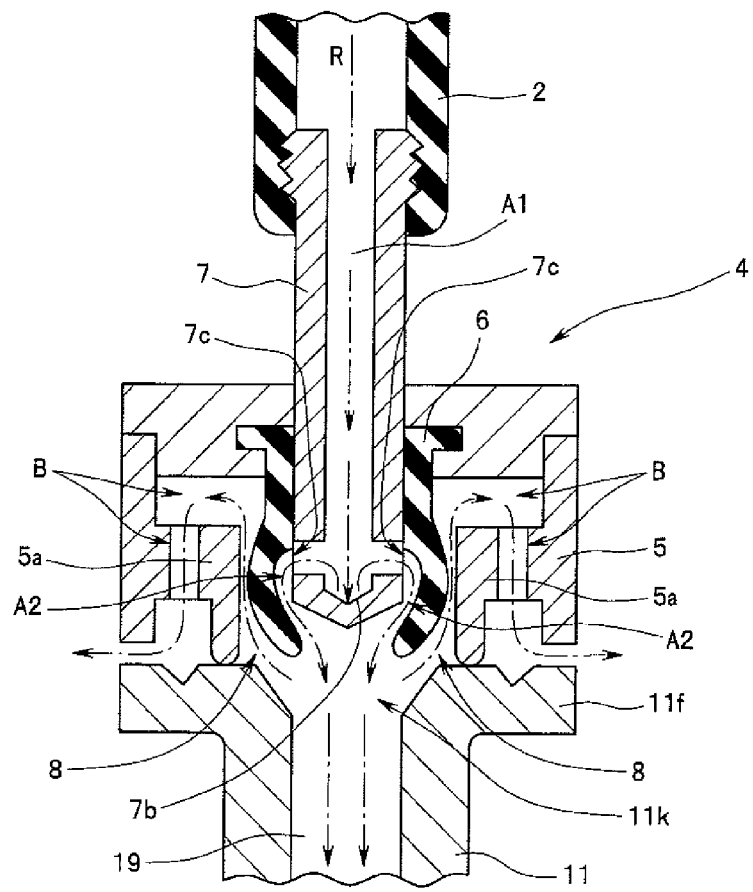
FIG. 2 is a partial cross-sectional view schematically illustrating a discharge section of the endoscope cleaning/disinfecting apparatus connector connected to a pipe sleeve of the endoscope in FIG. 1 when an opening/closing section is in a contracted state.

FIG. 1 is a diagram schematically illustrating an endoscope cleaning/disinfecting apparatus provided with an endoscope cleaning/disinfecting apparatus connector according to the present embodiment with an endoscope immersed in a liquid stored in a cleaning/disinfecting tank and FIG. 2 is a partial cross-sectional view schematically illustrating a discharge section of the endoscope cleaning/disinfecting apparatus connector connected to a pipe sleeve of the endoscope in FIG. 1 when an opening/closing section is in a contracted state.

Figure 3:
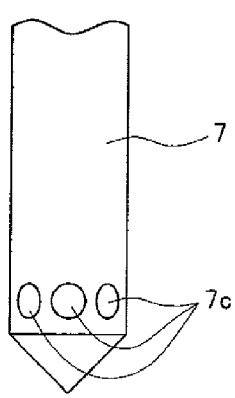
FIG. 3 is a partial plan view of a channel member in FIG. 2.
Figure 4:
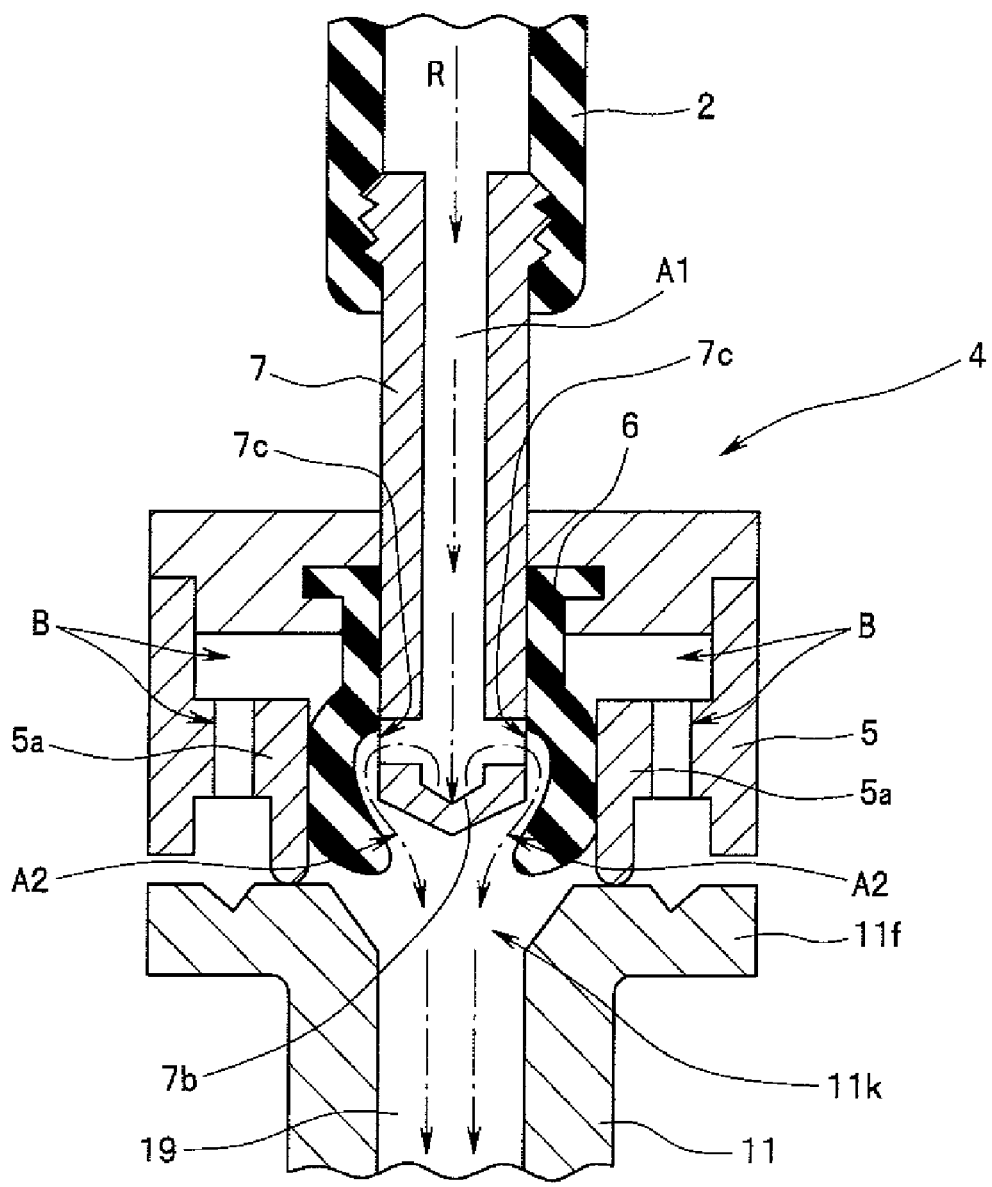
FIG. 4 is a partial cross-sectional view schematically illustrating the discharge section of the endoscope cleaning/disinfecting apparatus connector connected to the pipe sleeve of the endoscope in FIG. 1 when the opening/closing section is in an expanded state.

Furthermore, FIG. 3 is a partial plan view of a channel member in FIG. 2 and FIG. 4 is a partial cross-sectional view schematically illustrating the discharge section of the endoscope cleaning/disinfecting apparatus connector connected to the pipe sleeve of the endoscope in FIG. 1 when the opening/closing section is in an expanded state.

As shown in FIG. 1, an endoscope cleaning/disinfecting apparatus connector 1 is configured by including a cleaning/disinfecting apparatus connection section 3, a circulating section 2 and a discharge section 4 as principal components thereof. This endoscope cleaning/disinfecting apparatus connector 1 connects an endoscope 10 and an endoscope cleaning/disinfecting apparatus 100.

The cleaning/disinfecting apparatus connection section 3 is provided at one end of the circulating section 2. The cleaning/disinfecting apparatus connection section 3 is freely connectable to any one of an air/water supply/forceps port 133, a forceps raising port 134 and a water leak detection port 135, all of which will be described later (see FIG. 7 for all) provided on the apparatus body 200 of the cleaning/disinfecting apparatus 100.

One end of the circulating section 2 communicates with the cleaning/disinfecting apparatus connection section 3. The circulating section 2 is a region where a fluid R (illustrated as a liquid in FIG. 1) circulates, which is supplied from each of the ports 133 to 135 of the cleaning/disinfecting apparatus 100 to which the cleaning/disinfecting apparatus connection section 3 is connected.

Furthermore, the other end of the circulating section 2 communicates with the discharge section 4. As shown in FIG. 2 and FIG. 3, the discharge section 4 is freely connectable to a pipe sleeve 11 of an operation section 15 having an opening 11k (see FIG. 2 for all) that communicates with an endoscope tube 19 extending to an insertion portion 14, the operation section 15 and a universal cord 16 (see FIG. 7 for all) in the endoscope 10 and is intended to discharge the fluid R that passes through the circulating section 2 to the endoscope 10.

Examples of the endoscope tube 19 include a known suction tube and an air/water supply tube.

As shown in FIG. 2 and FIG. 4, the discharge section 4 is configured by including a connector body 5, a channel member 7, a half portion on a distal end side of which is inserted into the connector body 5 and which is connected to the other end of the circulating section 2 and an opening/closing section 6 which is freely attachable/detachable to/from an outer circumference of the channel member 7 in the connector body 5 as principal components thereof. Since the opening/closing section 6 is freely attachable/detachable to/from the outer circumference of the channel member 7, the opening/closing section 6 can be replaced easily.

The channel member 7 is formed of, for example, an elongated cylindrical member and a first channel A1 is formed inside the channel member 7. The first channel A1 communicates with the circulating section 2 and discharges the fluid R that passes through the circulating section 2 to the endoscope tube 19 via the interior of the pipe sleeve 11 of the endoscope 10, that is, the opening 11k.

Furthermore, a first water control section 7b that repels the flow of the fluid R introduced into the first channel A1 is formed at a distal end side of the first channel A1 of the channel member 7. Furthermore, as shown in FIG. 2 and FIG. 3, a plurality of openings 7c that communicate with the first channel A1 are formed at regular intervals along the outer circumferential direction of the channel member 7 on the outer circumferential side on the distal end side of the channel member 7. The fluid R introduced into the first channel A1 and repelled from the first water control section 7b is exhausted from the openings 7c.

When the discharge section 4 is connected to the pipe sleeve 11, the connector body 5 watertightly and airtightly contacts the top face of a flange section 11f of the pipe sleeve 11 and is fixed to the flange section 11f by a hooking member (not shown) or the like. When the discharge section 4 is connected to the pipe sleeve 11, the discharge section 4 is positioned with respect to the pipe sleeve 11 in this way.

Furthermore, as shown in FIG. 2 and FIG. 4, a second channel B is formed between the connector body 5 and the channel member 7 which branches from the first channel A1 and discharges the fluid that passes through the circulating section 2 and the first channel A1 to the periphery of the pipe sleeve 11.

Furthermore, in a branch section 8 that branches from the first channel A1 of the connector body 5 to the second channel B, a second water control section 5a that branches the fluid R exhausted from the opening 7c to the second channel B is provided at a position facing the opening 7c.

The opening/closing section 6 is formed of a freely expandable/contractible member such as fluorine rubber, silicon rubber and ethylene propylene rubber. As shown in FIG. 2 and FIG. 4, the opening/closing section 6 is located between the opening 7c and the second water control section 5a in the branch section 8 and formed, for example, into a curved shape so that the distal end side thereof does not block the opening 7c. The opening/closing section 6 may be located in the second channel B without being limited to be located in the branch section 8.

Furthermore, the distal end side of the opening/closing section 6 is in non-contact with the opening 7c of the channel member 7 and a region from the opening 7c to the distal end side, and because of this non-contact area, a first channel A2 is also formed between the distal end side of the opening/closing section 6 and a region from the opening 7c of the channel member 7 to the distal end side.

The opening/closing section 6 is in an expanded or contracted state according to the flow rate of the fluid R that flows through the first channels A1 and A2. That is, when the flow rate of the fluid R that flows through the first channels A1 and A2 exceeds a predetermined amount, the opening/closing section 6 expands from a contracted state in non-contact with the second water control section 5a as shown in FIG. 2, comes into contact with the second water control section 5a as shown in FIG. 4 and blocks the second channel B side while keeping the watertight and airtight state.

Hereinafter, a method of controlling the flow rate of the fluid R that causes the opening/closing section 6 to expand/contract will be described using FIG. 1.

As shown in FIG. 1, a circulation port 156 of a cleaning/disinfecting tank 50 in the apparatus body 200 of the cleaning/disinfecting apparatus 100 communicates with each of the ports 133 to 135 via a circulation tube 210 and a pump 221, a flow rate sensor 240 and a CH valve 231 are interposed in that order from the downstream side at midway positions of the circulation tube 210.

Furthermore, one end of a bypass tube 211 is connected to a position between the flow rate sensor 240 and the CH valve 231 in the circulation tube 210 with a bypass valve 232 provided at some midpoint. The other end of the bypass tube 211 is connected to an exhaust tube 212, one end of which is connected to an exhaust port 155 of the cleaning/disinfecting tank 50. An exhaust valve 233 and an exhaust pump 222 are interposed downstream of the connection region at the other end of the bypass tube 211 of the exhaust tube 212.

Therefore, when the fluid R is supplied to only the endoscope tube 19 using the first channels A1 and A2 without the fluid R leaking from the second channel B first, the pump 221 is driven by closing the bypass valve 232 and opening the CH valve 231.

As a result, the fluid R in the cleaning/disinfecting tank 50 flows from the circulation port 156 through the circulation tube 210 from the respective ports 133 to 135 to the cleaning/disinfecting apparatus connection section 3, the circulating section 2 and the discharge section 4, and is supplied into the endoscope tube 19 via the first channels A1 and A2, and the opening 11k.

In this case, when the flow rate of the fluid R that flows through the first channel A2 exceeds a predetermined flow rate, as shown in FIG. 4, the fluid R that flows through the first channel A2 causes the opening/closing section 6 to expand and contact the second water control section 5a watertightly and airtightly, and therefore the fluid R does not flow into the second channel B but is supplied into only the endoscope tube 19.

Thus, the case where the fluid R is supplied by causing the opening/closing section 6 to expand is suitable for high pressure cleaning of the endoscope tube 19 and cleaning using a gas/liquid two-phase flow or the like.

Next, the case where not only the endoscope tube 19 but also the pipe sleeve 11 and the periphery of the pipe sleeve 11 are cleaned/disinfected by causing the fluid R to leak from the second channel B, the CH valve 231 is opened and the bypass valve 232 is opened.

As a result, as described above, the fluid R that flows through the circulation tube 210 flows from the ports 133 to 135 to the cleaning/disinfecting apparatus connection section 3, the circulating section 2 and the discharge section 4 and is supplied into the endoscope tube 19 through the first channels A1 and A2, and the opening 11k, and also a part thereof flows through the bypass tube 211. In this case, if the exhaust valve 233 is closed, the fluid R flowing through the bypass tube 211 is resupplied into the cleaning/disinfecting tank 50 from the exhaust port 155 through the exhaust tube 212.

Thus, the flow rate of the fluid R that flows through the first channels A1 and A2 is smaller than when the bypass valve 232 is closed and is also smaller than the predetermined flow rate, and therefore as shown in FIG. 2, the opening/closing section 6 contracts and the fluid R also flows through the second channel B. As a result, the fluid R is also supplied to the periphery of the pipe sleeve 11.

For this reason, the case where the opening/closing section 6 is caused to contract is suitable for cleaning/disinfecting of the pipe sleeve 11 and the periphery of the pipe sleeve 11 in addition to normal cleaning/disinfecting of the endoscope tube 19.

As described above, by switching the opening/closing of the bypass valve 232, it is possible to cause the opening/closing section 6 to expand/contract. That is, it is possible to select whether the fluid R is supplied into only the endoscope tube 19 or into not only the endoscope tube 19 but also the periphery of the pipe sleeve 11.

The method of controlling the flow rate of the fluid R by causing the opening/closing section 6 to expand/contract is not limited to the opening/closing of the bypass valve 232, but other techniques may also be used. For example, the pump 221 may be used to differentiate the amount of the fluid R supplied to the first channels A1 and A2 in the first place.

Thus, according to the present embodiment, the endoscope cleaning/disinfecting apparatus connector 1 is provided with the opening/closing section 6 that expands/contracts according to the flow rate of the fluid R around the outer circumference of the channel member 7 of the discharge section 4 connected to the pipe sleeve 11 of the endoscope 10 and the opening/closing section 6 is located in the branch section 8 from the first channels A1 and A2 to the second channel B or in the second channel B.

According to this, when the fluid R is supplied only into the endoscope tube 19, the flow rate of the fluid R that flows through the first channels A1 and A2 is set to a predetermined amount or higher, and therefore the opening/closing section 6 expands, contacts the second water control section 5a and blocks the second channel B, making it possible to supply the fluid R only into the endoscope tube 19.

Furthermore, when the fluid R is supplied not only into the endoscope tube 19 but also to the periphery of the pipe sleeve 11, the flow rate of the fluid R that flows through the first channels A1 and A2 is set to be smaller than the predetermined amount, and the opening/closing section 6 is thereby caused to contract and the second channel B is produced between the opening/closing section 6 and the second water control section 5a, and it is thereby possible to supply the fluid R not only into the endoscope tube 19 but also to the periphery of the pipe sleeve 11 via the second channel B.

That is, whether to block the second channel B or not as the opening/closing section 6 expands or contracts can be determined using a simple configuration of changing the amount of supply of the fluid R.

As described above, it is possible to provide the endoscope cleaning/disinfecting apparatus connector 1 and the endoscope cleaning/disinfecting apparatus 100 in a simple configuration capable of switching between a case where only the interior of the endoscope tube 19 is cleaned/disinfected and a case where not only the interior of the endoscope tube 19 but also the pipe sleeve 11 and the periphery of the pipe sleeve 11 of the endoscope 10 are cleaned/disinfected.

(Second Embodiment)

Figure 5:
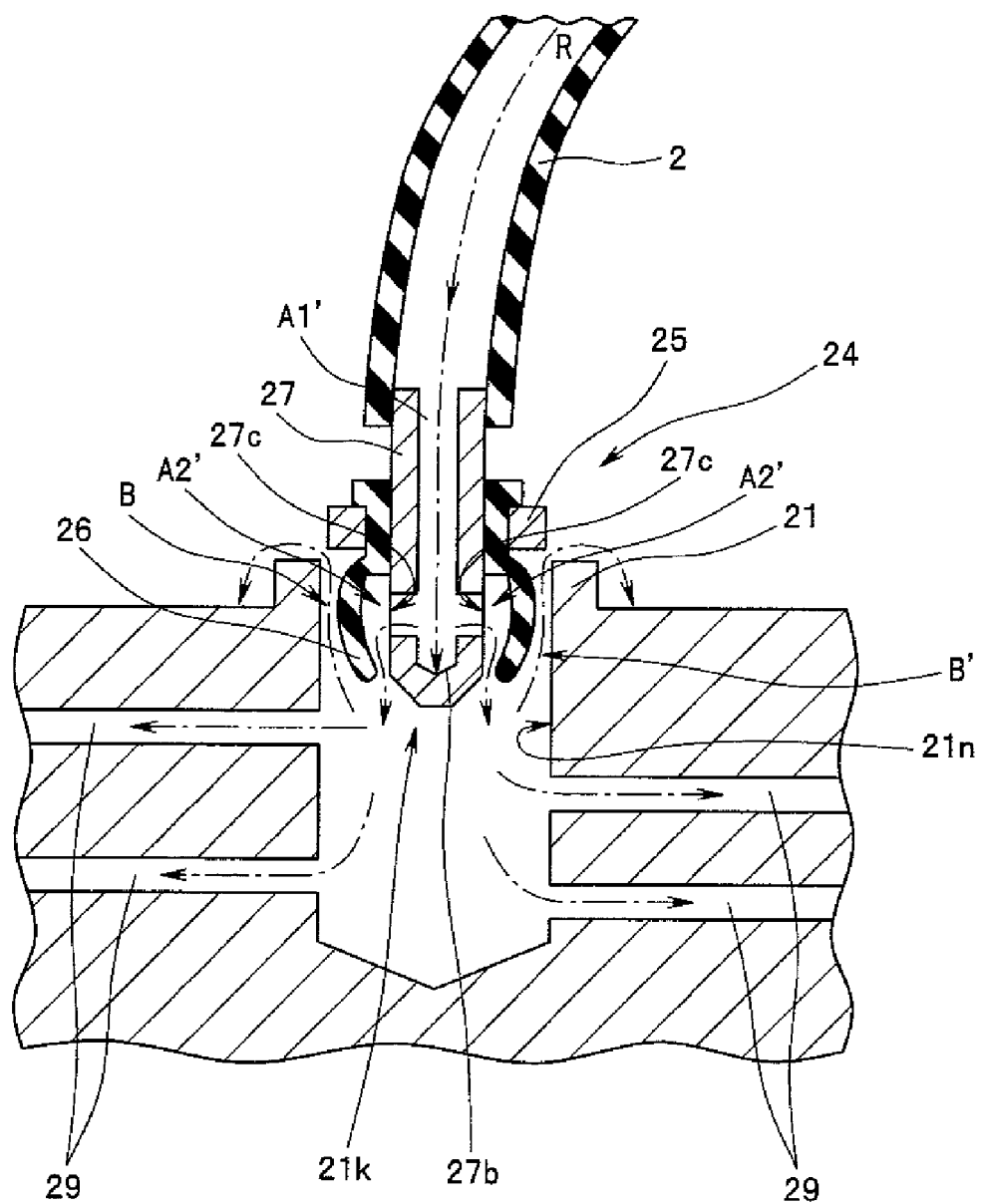
FIG. 5 is a partial cross-sectional view schematically illustrating the discharge section of the endoscope cleaning/disinfecting apparatus connector according to an embodiment connected to the pipe sleeve of the endoscope when the opening/closing section is in a contracted state.

FIG. 5 is a partial cross-sectional view schematically illustrating the discharge section of the endoscope cleaning/disinfecting apparatus connector according to the present embodiment connected to the pipe sleeve of the endoscope when the opening/closing section is in a contracted state.

Figure 6:
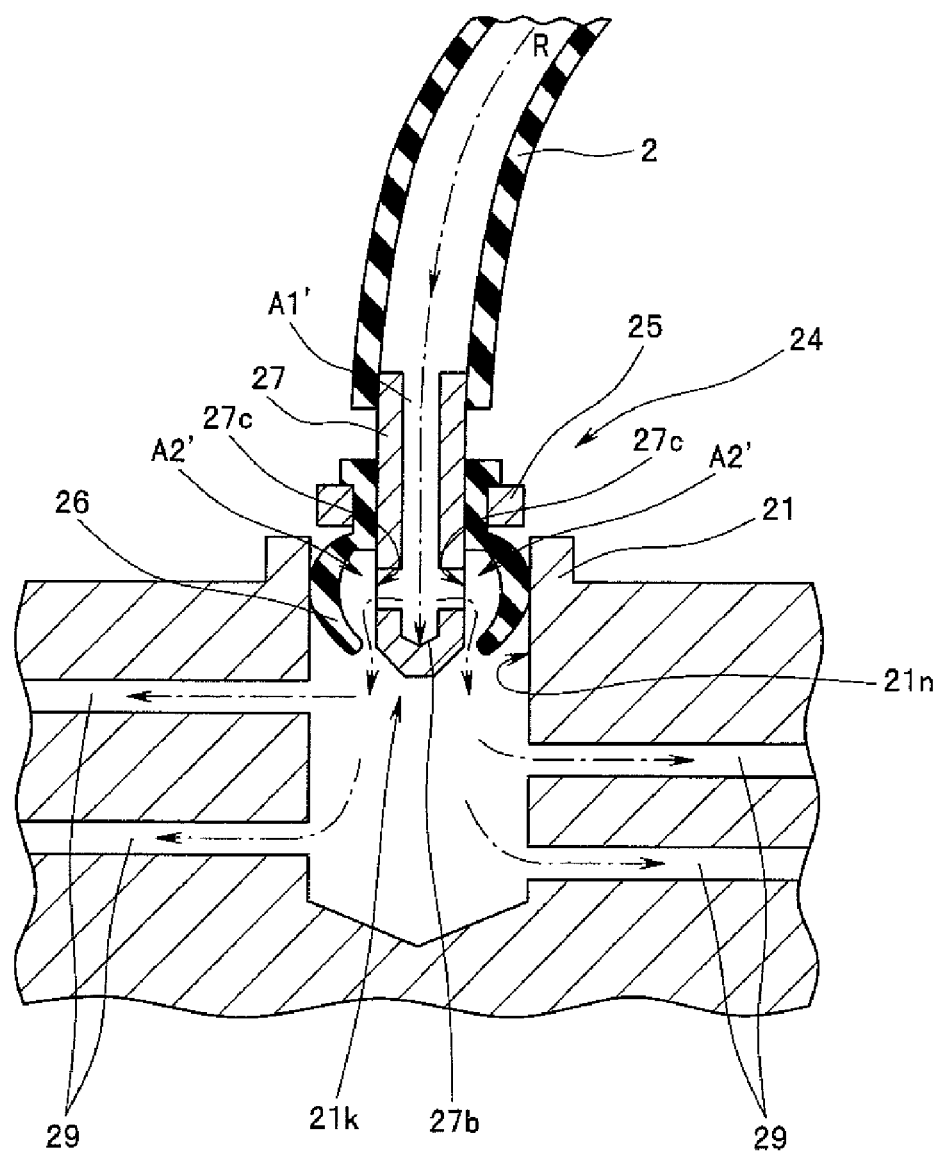
FIG. 6 is a partial cross-sectional view schematically illustrating the discharge section of the endoscope cleaning/disinfecting apparatus connector connected to the pipe sleeve of the endoscope when the opening/closing section is in an expanded state.

Furthermore, FIG. 6 is a partial cross-sectional view schematically illustrating the discharge section of the endoscope cleaning/disinfecting apparatus connector connected to the pipe sleeve of the endoscope when the opening/closing section is in an expanded state.

The configuration of the endoscope cleaning/disinfecting apparatus connector and the endoscope cleaning/disinfecting apparatus of this second embodiment is different from the endoscope cleaning/disinfecting apparatus connector and the endoscope cleaning/disinfecting apparatus of the aforementioned first embodiment shown in FIG. 1 to FIG. 4 in that the discharge section of the endoscope cleaning/disinfecting apparatus connector is connected by being inserted in the pipe sleeve. Therefore, only this difference will be described and the same components as those in the first embodiment will be assigned the same reference numerals and descriptions thereof will be omitted.

As shown in FIG. 5 and FIG. 6, the endoscope cleaning/disinfecting apparatus connector according to the present embodiment is also intended to connect the endoscope 10 and the endoscope cleaning/disinfecting apparatus 100 and is configured by including a cleaning/disinfecting apparatus connection section 3 (not shown), a circulating section 2 and a discharge section 24 as principal components thereof.

The discharge section 24 is provided in communication with the other end of the circulating section 2 and freely connectable to a pipe sleeve 21 of an operation section 15 having an opening 21k communicating with an endoscope tube 29 that extends to an insertion portion 14, the operation section 15 and a universal cord 16 (see FIG. 7 for all) in the endoscope 10. Examples of the pipe sleeve 21 include a forceps port 37 (see FIG. 7) provided in the operation section 15 of the endoscope 10.

Furthermore, when connected to the pipe sleeve 21, the discharge section 24 is positioned by being inserted in the pipe sleeve 21 through the opening 21k. Thus, the discharge section 24 discharges the fluid R that passes through the circulating section 2 to the endoscope 10. Examples of the endoscope tube 29 include a known suction tube and an air/water supply tube.

The discharge section 24 is configured by including a connector body 25, a channel member 27, a half part of the distal end side of which is inserted into the connector body 25 and connected to the other end of the circulating section 2, and an opening/closing section 26 freely attachable/detachable to/from an outer circumference of the channel member 27 inside the connector body 25 as principal components thereof. Since the opening/closing section 26 is freely attachable/detachable to/from the outer circumference of the channel member 27, the opening/closing section 26 can be easily replaced.

The channel member 27 is formed of, for example, an elongated cylindrical member and internally communicates with the circulating section 2 and is provided with a first channel A1' that discharges the fluid R that passes through the circulating section 2 to the endoscope tube 29 via the interior of the pipe sleeve 21 of the endoscope 10, that is, the opening 21k.

Furthermore, a water control section 27b which repels the flow of the fluid R introduced into a first channel A1' is formed on the distal end side of the first channel A1' of the channel member 27. A plurality of openings 27c are formed on the outer circumferential side on the distal end side of the channel member 27 which exhaust the fluid R repelled by the water control section 27b from the first channel A1' and communicate with the first channel A1' along the outer circumferential direction of the channel member 27 at regular intervals.

The opening/closing section 26 is located between the channel member 27 inserted in the pipe sleeve 21 and an inner wall 21n of the pipe sleeve 21, made of a freely expandable/contractible member such as fluorine rubber, silicon rubber, ethylene propylene rubber and formed into, for example, a curved shape so that the distal end side thereof does not block the opening 27c as shown in FIG. 5 and FIG. 6.

The distal end side of the opening/closing section 26 is in non-contact with the opening 27c of the channel member 27 and a region from the opening 27c to the distal end side, and a first channel A2' is also formed between the distal end side of the opening/closing section 26 and a region from the opening 27c of the channel member 27 to the distal end side.

Furthermore, a second channel B' is formed between the inner wall 21n of the pipe sleeve 21 and the channel member 27, which branches from the first channel A1' and discharges the fluid R that passes through the circulating section 2 and the first channel A1' to the periphery of the pipe sleeve 21. The opening/closing section 26 is freely expandable/contractible according to the flow rate of the fluid R that flows through the first channels A1' and A2' as shown in FIG. 5 and FIG. 6 as in the case of the aforementioned first embodiment, and when the flow rate of the fluid R that flows through the first channels A1' and A2' exceeds a predetermined amount, the state changes from a contracted state in which the opening/closing section 26 is in non-contact with the inner wall 21n of the pipe sleeve 21 shown in FIG. 5 to a state as shown in FIG. 6 in which the opening/closing section 26 comes into contact with the inner wall of the pipe sleeve 21 watertightly and airtightly thus blocking the second channel B' as the opening/closing section 26 expands.

A method of controlling the flow rate of the fluid R that causes the opening/closing section 26 to expand/contract is the same as that in the case of causing the opening/closing section 6 to expand/contract according to the aforementioned first embodiment, and therefore descriptions thereof will be omitted.

Thus, the present embodiment has shown that when connected to the pipe sleeve 21, the discharge section 24 of the endoscope cleaning/disinfecting apparatus connector is inserted into the pipe sleeve 21 and the opening/closing section 26 provided in the discharge section 24 that expands/contracts according to the flow rate of the fluid R, is attached to the channel member 27 so as to be located between the channel member 27 and the inner wall 21n of the pipe sleeve 21.

Thus, when the fluid R is supplied only into the endoscope tube 29, the flow rate of the fluid R that flows through the first channels A1' and A2' is set to a predetermined amount or higher and the opening/closing section 26 thereby expands, comes into contact with the inner wall 21n of the pipe sleeve 21 and blocks the second channel B', and can thereby supply the fluid R only into the endoscope tube 29.

Furthermore, when the fluid R is supplied not only into the endoscope tube 29 but also to the periphery of the pipe sleeve 21, the flow rate of the fluid R that flows through the first channels A1' and A2' is set to be smaller than the predetermined amount, and the opening/closing section 26 thereby contracts and the second channel B' is produced between the opening/closing section 26 and the inner wall 21n of the pipe sleeve 21, and therefore the fluid R can be supplied not only into the endoscope tube 29 but also to the periphery of the pipe sleeve 21 via the second channel B'.

As described above, the present embodiment can also obtain effects similar to those of the aforementioned first embodiment.

The configuration of the discharge section 24 of the second embodiment can be used only when a sufficient space for the discharge section 24 to be inserted can be secured inside the pipe sleeve 21 and the opening/closing section 26 does not contact the opening of the endoscope tube 29 formed in the inner wall 21n inside the pipe sleeve 21.

This is because in the configuration in which the opening/closing section 26 contacts the opening of the endoscope tube 29 inside the pipe sleeve 21 when the opening/closing section 26 expands in the pipe sleeve 21, the opening/closing section blocks the opening of the endoscope tube 29 when the opening/closing section 26 expands in the pipe sleeve 21 and thereby prevents the fluid R from being supplied to the blocked endoscope tube 29.

Figure 7:
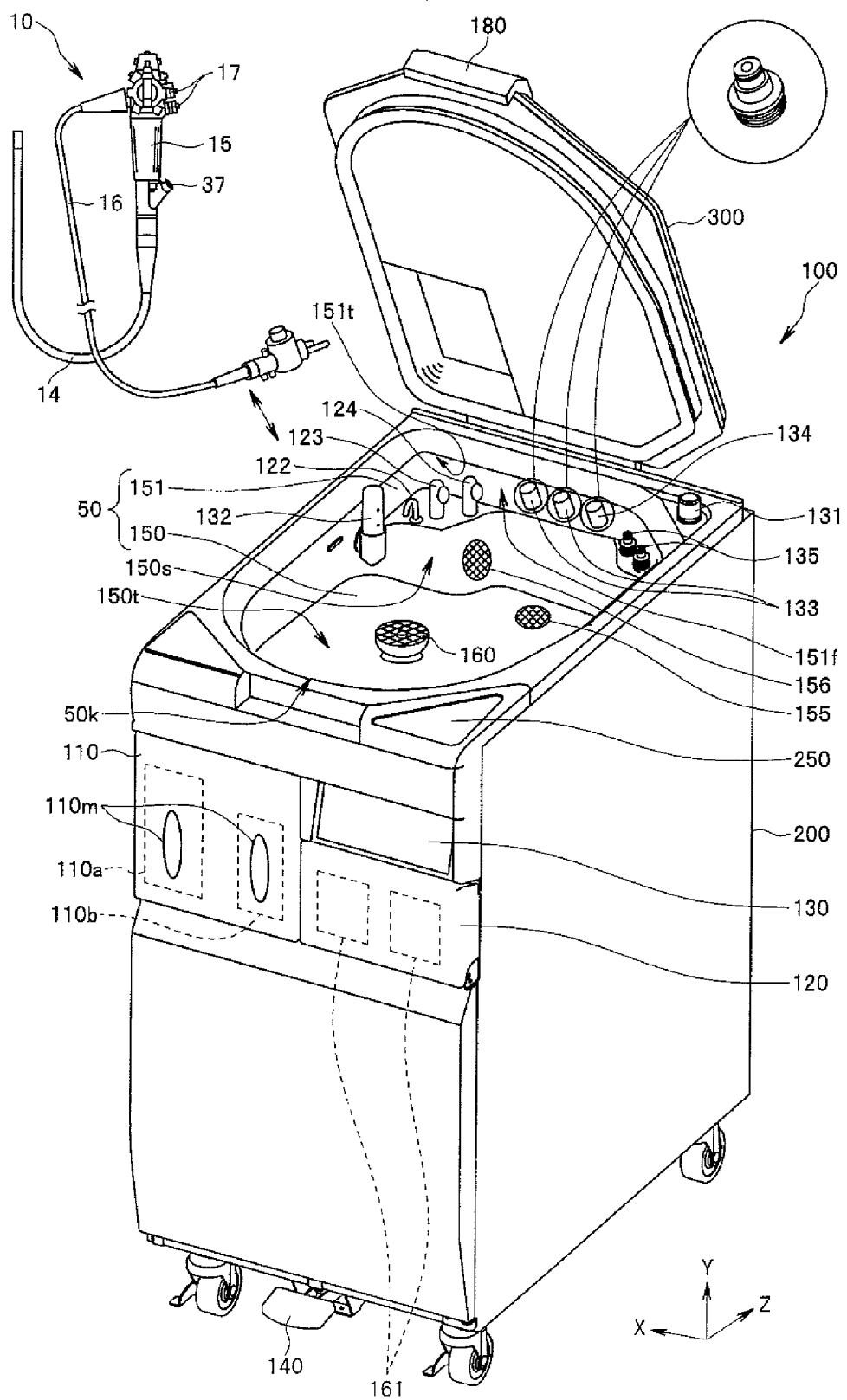
FIG. 7 is a perspective view illustrating an example of the endoscope cleaning/disinfecting apparatus together with the endoscope.

Next, an example of the cleaning/disinfecting apparatus 100 to which the cleaning/disinfecting apparatus connection section 3 of the aforementioned endoscope cleaning/disinfecting apparatus connector according to the first to second embodiments can be freely connected will be described using FIG. 7. FIG. 7 is a perspective view illustrating an example of the endoscope cleaning/disinfecting apparatus together with the endoscope.

As shown in FIG. 7, the endoscope cleaning/disinfecting apparatus 100 is an apparatus for cleaning or disinfecting the endoscope 10 after use and principal parts thereof are configured of an apparatus body 200 and a top cover 300 provided thereon which is a cover body connected thereto in a freely openable/closable manner via, for example, a hinge (not shown).

An accommodation section (not shown) is formed on the front (hereinafter referred to as "front") in the figure in proximity to an operator of the apparatus body 200 and, for example, in an upper part in the height direction Y of the left-half part in the width direction X of the apparatus body 200 and a detergent/alcohol tray 110 is disposed in the accommodation section in a manner freely drawable forward from the apparatus body 200. Hereinafter, the direction connecting the front and the rear of the apparatus body 200 will be referred to as "depth direction Z" in the figure.

The detergent/alcohol tray 110 accommodates a detergent tank 110a that stores a detergent used to clean the endoscope 10 and an alcohol tank 110b that stores alcohol which is a liquid used to dry the endoscope 10 after cleaning/disinfection, and since the detergent/alcohol tray 110 is freely drawable forward in the depth direction Z, the liquid can be replenished to a predetermined level to each tank 110a or 110b.

The detergent/alcohol tray 110 is provided with two window sections 110m and the window sections 110m allow the operator to check the remaining amounts of detergent and alcohol stored in the tanks 110a and 110b. The detergent is a concentrated detergent that is diluted to a predetermined concentration with tap water filtered through a feed water filter (not shown).

Furthermore, a cassette tray 120 is disposed on the front of the apparatus body 200, for example, in an upper part in the height direction Y of the right-half section in the width direction X in a manner freely drawable forward in the depth direction Z of the apparatus body 200. The cassette tray 120 stores a disinfecting liquid cassette 161 used to disinfect the endoscope 10.

Since the cassette tray 120 is freely drawable, it is possible to set the disinfecting liquid cassette 161 in a predetermined way.

Furthermore, a sub-operation panel 130 is disposed on the front of the apparatus body 200 in an upper part in the height direction Y of the cassette tray 120 on which a display of the cleaning/disinfecting time and a button for instructing heating of the disinfecting liquid or the like are arranged.

Furthermore, a pedal switch 140 is disposed in a lower part in the height direction Y on the front of the apparatus body 200 for the operator to step thereon to cause the top cover 300 in the closed position on the apparatus body 200 to open upward of the apparatus body 200.

Furthermore, a main operation panel 250 is provided, for example, near both sides in the width direction X on the front side in the depth direction Z in proximity to the operator on the top surface in the height direction Y of the apparatus body 200, provided with setting switches such as cleaning/disinfecting operation start switch, and cleaning/disinfecting mode selection switch of the apparatus body 200 or a switch to select one or both of the endoscope tubes 19 and 29 and pipe sleeves 11 and 21 to be cleaned/disinfected.

Furthermore, a feed water hose connection port 131 is disposed on the top surface in the height direction Y of the apparatus body 200 and on the rear side facing the front in proximity to the operator in the depth direction Z to supply tap water to the apparatus body 200 to which a feed water hose connected to the faucet is connected. A mesh filter for filtering tap water may also be attached to the feed water hose connection port 131.

Furthermore, a cleaning/disinfecting tank 50 is provided in substantially the center on the top surface in the height direction Y of the apparatus body 200 in which the endoscope 10 can be freely accommodated, an endoscope accommodation cavity of which is opened/closed with the top cover 300. The cleaning/disinfecting tank 50 is made up of a tank body 150 and a terrace section 151 continuously provided around the outer perimeter of the endoscope accommodation cavity of the tank body 150.

When the endoscope 10 after use is cleaned/disinfected, the tank body 150 can freely accommodate the endoscope 10 and a bottom surface 150t which is a surface inside the tank of the tank body 150 is provided with an exhaust port 155 to exhaust the cleaning liquid, water, alcohol, disinfecting liquid or the like supplied to the tank body 150 from the tank body 150 or return the disinfecting liquid to the disinfecting liquid tank or return the fluid R flown from the aforementioned bypass tube 211 via the exhaust tube 212 to the cleaning/disinfecting tank 50.

Furthermore, a circulation port 156 is provided at an arbitrary position on a peripheral side surface 150s which is a surface inside the tank of the tank body 150 to supply the cleaning liquid, water, disinfecting liquid or the like supplied to the tank body 150 to the endoscope tubes 19 and 29 provided inside the endoscope 10 via means (not shown) or resupply them from a feed water circulation nozzle 124 to the tank body 150 via a mesh filter or the like. The circulation port 156 may be provided with a mesh filter for filtering the cleaning liquid or the like.

The aforementioned circulation port 156 may also be provided on the bottom surface 150t of the tank body 150.

The provision of the circulation port 156 on the bottom surface 150t of the tank body 150 can advance the timing of supplying the cleaning liquid, water, disinfecting liquid or the like to each tube of the endoscope 10 or resupplying them to the tank body 150. Furthermore, when the user replaces the mesh filter or the like provided on the circulation port 156, there is an advantage that the operator can easily approach the mesh filter provided on the bottom surface.

A cleaning case 160 is disposed in substantially the center of the bottom surface 150t of the tank body 150 of the cleaning/disinfecting tank 50.

The cleaning case 160 accommodates buttons of scope switches 17 or the like of the endoscope 10 and removable parts disposed together with the endoscope 10. As a result, the buttons and removed parts are cleaned and disinfected together with the endoscope 10.

A water level sensor 132 with a cover is provided at an arbitrary position of the side surface 150s of the tank body 150 for detecting the level of the cleaning liquid, water, disinfecting liquid or the like supplied to the tank body 150.

A detergent nozzle 122 for supplying a detergent from the detergent tank 110a diluted to a predetermined concentration with tap water to the tank body 150 by means of a detergent pump (not shown) and a disinfecting liquid nozzle 123 for supplying a disinfecting liquid from a disinfecting liquid tank which will be described later by means of a disinfecting liquid feed pump are disposed on a surface other than the terrace surface 151t of the terrace section 151, that is, a surface parallel to the bottom surface 150t of the tank body 150.

Moreover, a feed water circulation nozzle 124 for supplying water to the tank body 150 or for resupplying the cleaning liquid, water, disinfecting liquid or the like suctioned from the circulation port 156 of the tank body 150 to the tank body 150 is disposed on the surface parallel to the bottom surface 150t of the tank body 150 of the terrace section 151.

The detergent nozzle 122, the disinfecting liquid nozzle 123 and the feed water circulation nozzle 124 may also be disposed on the terrace surface 151t.

Furthermore, a plurality of (here 2) air/water supply/forceps ports 133 for supplying the cleaning liquid, water, alcohol, disinfecting liquid, air, or the like to the endoscope tubes 19 and 29, a forceps raising port 134 and a water leak detection port 135 are disposed on a surface 151f on the side opposite to a position 50k in proximity to the operator of the terrace surface 151t of the terrace section 151.

Furthermore, the pipe sleeve 11 of the operation section 15 of the aforementioned endoscope 10 is exposed after each scope switch 17 is removed from the operation section 15.

The configuration of the endoscope cleaning/disinfecting apparatus is not limited to the configuration in FIG. 7.

The aforementioned endoscope cleaning/disinfecting apparatus 100 has been described as an apparatus that cleans or disinfects the endoscope 10, but it goes without saying that the endoscope cleaning/disinfecting apparatus 100 can also clean or disinfect other medical instruments such as a treatment instrument.

What is claimed is:

1. An endoscope cleaning/disinfecting apparatus connector that connects an endoscope and an endoscope cleaning/disinfecting apparatus, comprising:
   a cleaning/disinfecting apparatus connection section connected to the endoscope cleaning/disinfecting apparatus;
   a circulating section, one end of which communicates with the cleaning/disinfecting apparatus connection section, and in which a fluid supplied from the cleaning/disinfecting apparatus circulates; and
   a discharge section that is provided at another end of the circulating section, is freely connectable to a pipe sleeve of the endoscope, remains inside the pipe sleeve after the connection and thereby discharges the fluid which passes through the circulating section to the endoscope,
   wherein the discharge section comprises:
   a first channel that communicates with the circulating section and discharges the fluid that passes through the circulating section into the pipe sleeve of the endoscope; and
   an opening/closing section that is provided to be positioned between the first channel and an inner wall of the pipe sleeve when the discharge section and the pipe sleeve are connected, the opening/closing section being freely expandable/contractible according to a flow rate of the fluid, expanding when the flow rate of the fluid is a predetermined amount or higher, and closing a second channel that is formed between the first channel and the inner wall of the pipe sleeve and discharges the fluid discharged from the first channel to a periphery of the pipe sleeve of the endoscope, and
   the discharge section comprises:
   a water control section that is provided in the first channel and repels the flow of the fluid; and
   an opening that is provided in the first channel and exhausts the fluid repelled by the water control section.

2. The endoscope cleaning/disinfecting apparatus connector according to claim 1, wherein the first channel is provided inside a channel member connected to the other end of the circulating section provided in the discharge section, and
   the opening/closing section is freely attachable or detachable with respect to the channel member.

* * * * *